United States Patent
Zheng

(10) Patent No.: US 9,854,823 B2
(45) Date of Patent: Jan. 2, 2018

(54) METHOD OF PROCESSING ANIMAL SKIN

(71) Applicant: Jingmin Zheng, Wenzhou (CN)

(72) Inventor: Jingmin Zheng, Wenzhou (CN)

(*) Notice: Subject to any disclaimer, the term of this patent is extended or adjusted under 35 U.S.C. 154(b) by 1416 days.

(21) Appl. No.: 13/655,744

(22) Filed: Oct. 19, 2012

(65) Prior Publication Data
US 2013/0040001 A1 Feb. 14, 2013

Related U.S. Application Data

(63) Continuation-in-part of application No. 11/789,570, filed on Apr. 25, 2007, now abandoned.

(30) Foreign Application Priority Data

Nov. 23, 2006 (CN) .......................... 2016 1 0145930

(51) Int. Cl.
| | | |
|---|---|---|
| *A23K 10/26* | (2016.01) | |
| *A23K 50/42* | (2016.01) | |
| *A23K 50/40* | (2016.01) | |

(52) U.S. Cl.
CPC .............. *A23K 50/42* (2016.05); *A23K 10/26* (2016.05); *A23K 50/40* (2016.05)

(58) Field of Classification Search
CPC ..................................................... A23K 10/26
See application file for complete search history.

(56) References Cited

U.S. PATENT DOCUMENTS

| | | | | |
|---|---|---|---|---|
| 3,494,773 A | * | 2/1970 | Bradshaw | A22C 13/0013 426/140 |
| 5,411,887 A | * | 5/1995 | Sjolander | C07K 14/78 435/273 |
| 5,968,568 A | * | 10/1999 | Kuraishi | A23J 3/06 426/302 |
| 6,500,473 B1 | * | 12/2002 | Koehler | A23L 2/58 426/540 |
| 2005/0249839 A1 | * | 11/2005 | Ishida | C12Y 203/02013 426/56 |
| 2008/0248167 A1 | * | 10/2008 | McMindes | A23L 13/424 426/92 |

FOREIGN PATENT DOCUMENTS

WO    WO 03017770 A1 *  3/2003 ......... A22C 13/0016

OTHER PUBLICATIONS

Mukhtar et al. "Tea Polyphenols: prevention of cancer and optimizing health". Am J Clin Nutr 2000; 71 (suppl): pp. 1698S-1702S.*

* cited by examiner

*Primary Examiner* — Jenna A Watts

(57) ABSTRACT

The present invention provides a method of processing animal skin, comprising the steps of: 1) providing dry animal skin containing 7-38 wt % water; 2) rehydrating and softening the said dry animal skin, and obtaining softened wet skin; 3) mixing the said softened wet skin with water, and grinding the mixture to a slurry; 4) obtaining a solid product through a crosslink of collagen proteins in the said slurry; wherein, rehydrating the said dry animal skin is performed through soaking the dry animal skin in 0-55° C. water till the animal skin contains 40-50 wt % water; and softening the said dry animal skin comprises a step of heating the rehydrated dry animal skin.

13 Claims, 2 Drawing Sheets

METHOD OF PROCESSING ANIMAL SKIN

CROSS-REFERENCE TO RELATED APPLICATIONS

This application is a continuation-in-part of U.S. patent application Ser. No. 11/789,570, filed Apr. 25, 2007, incorporated herein by reference.

FIELD OF THE INVENTION

This invention relates to a method of processing animal skin and the products produced by this method.

BACKGROUND OF THE INVENTION

In mammalian skin, collagen is the most abundant structural constituent of the dermis, comprising of about three quarters of the dry weight of this part of the integument. The arrangement and tensile strength of the fibers and fiber bundles formed by this scleroprotein give the skin the ability to resist the mechanical stresses of tension and pressure. The limited elasticity, extensibility, tension and the shock absorption capacity of the skin depend on a three dimensional network of the collagen fibers and fiber bundles.

Collagen fibrils are made of many individual collagen molecules packed together, Each collagen molecule is a triple helix, three protein chains, each of which is a left-handed helix form and stable right-handed super-helix by hydrogen-bond, twisted together in a specific shape to form a sturdy, stable protein strand. When the water content of animal skin is relatively low, collagen protein is very stable and cannot be decomposed by heating at normal temperatures in a short time. However in high water content, the collagen protein can be denatured by heating. In this state, hydrolytic cleavage of covalent bond loosen the hydrogen bond or static bond in the collagen protein, and the three tropocollagen strands will be separated partially or completely into globular domains, containing a different, secondary, structure to the normal collagen polyproline II (PPII), e.g. random coils, i.e. collagen is denatured into gelatin. It is difficult to reorganize the modified animal skin into new skin with similar features such as glutinosity, flexibility and tensile properties as natural skin.

For years people have produced artificial collagen membranes and casings with modified natural animal collagen. So far, the major source of the animal collagen has been from bovine collagen from bovine hide. After butchering the cow and peeling off the skin, the underlayer of bovine collagen will be separated and mechanically transformed into a gel. The reformed gel will be further extruded to form casings, and subsequently the casings will be solidified, typically by adjusting the pH and/or applying a cross linker e.g. glutaraldehyde. However, pig collagen is seldom used to produce artificial collagen casings, or artificial skin, mainly because of the low tensile strength of the product.

The general method for producing artificial animal skin using pig skin usually includes the next steps: (1) washing the skin with alkali; (2) grinding the skin; (3) adding additives such as polyvinyl alcohol aldehyde condensation compound, etc., and (4) extruding the mixture into shapes and obtaining tubular casings by a method of pushing and bath-law concreting. Through this method, a 0.03-0.1 mm sausage casing is finally produced in a sequenced process of drying, modifying, folding or shrinking.

T. Morgan also disclosed a method (Chinese Patent Application No. 02816630.2) of extruding the gel containing pig collagen, fat and moisturizing agent to produce tubular casings for foods (e.g. sausage). However, this method is relatively complicated: firstly, it comprises a step of adjusting the proportions of collagen, fat and moisturizing agent in the materials, and secondly, it is a complicated de-fatting process.

In view of the above mentioned defects in prior art, this invention is dedicated to provide a new method of producing products with sufficient tensile strength using animal skin, especially pig skin. The products can be used as pet foods, e.g. dog foods, or pet toys, or packaging materials.

SUMMARY OF THE INVENTION

One aspect of the invention is to provide a new method of processing animal skin, comprising the steps of:
1) providing a dry animal skin with 7-38 wt % water content;
2) rehydrating and softening the dry animal skin to obtain a softened wet skin;
3) mixing the softened wet skin with water to obtain a mixture, and grinding the mixture to a slurry;
4) obtaining a solid product through crosslink of collagen proteins in the slurry;
wherein, the said rehydrating in step 2) is done by soaking the dry animal skin in 0-55° C. water until the water content of the animal skin reaches 40-50 wt % to obtain a rehydrated animal skin; and the said softening in step 2) comprises a step of heating the rehydrated animal skin.

Another aspect of the invention is to provide a pet food or pet toy, which is made from the solid product created by the method of processing animal skin in this invention.

The method of processing animal skin in this invention is simple and convenient to carry out and the flexibility and strength of the final manufactured product are as good as the natural animal skins.

DESCRIPTION OF THE PREFERRED EMBODIMENT

Figure 1:
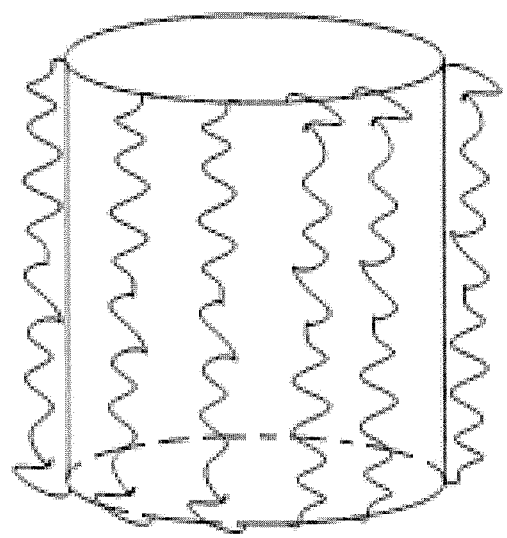
FIG. 1 is a diagram of the pet toy provided in a preferred embodiment in the invention.

While the applicant was exploring ways to use the animal skins, especially pigskin, to produce products with improved strength, the applicant got some unexpected surprising discoveries. The applicant found that the fat content in raw materials of animal skin has significant influences on the strength of final artificial skin products and the strength of the products will be improved greatly when the fat content in animal skin is reduced as much as possible. On this basis, it has been reported that some inventors defatted animal skin when producing casing. The applicant found that dry skin generated in the process of manufacturing animal skin-related products can be used directly to produce the product of this invention. Herein, the "dry skin" refers to animal skin that is defatted and dried but contains collagenous fibers. The dry animal skin may be any one of bovine hide, horsehide, sheepskin, pigskin, donkeyskin, etc. Typically, the water content of these dry skins is among 7-38 wt %. The applicant found that these dry skins can be used as raw materials to produce artificial skin products which have a flexibility and tensile strength as good as natural skins.

A challenge of using these dry skins as raw materials to produce artificial skins is how to rehydrate and soften the skins, and how to break the structure of original collagen protein. Collagen is composed of three to four polypeptide chains with a width of about 3 nm. Although the triple helix structure of collagen is very stable, the terminal peptides connecting to the triple helix structure are unstable. The applicant found that collagen protein molecular chains maybe destroyed by a moderate heat treatment, which will cause degeneration of collagen protein and make it easy to be grinded. The interaction amongst atoms or molecules including hydrogen bonds, Van der Waals attraction and hydrophobic bonds will be weakened rapidly by heat treatment and the triple helix structure of collagen protein will be destroyed. Even the collagen peptide train will be broken and then the skin will be softened. The applicant also found the expected result by softening using hot steam, which is very convenient, to treat rehydrated dry skin. It is preferred to heat the rehydrated dry skin by hot steam at 100-125° C. for 5-45 min.

The applicant also found that too much rehydration of the dry skin will result in much of the collagen being converted into gelatin in the following heat treatment step, which is unexpected. If the conversion ratio of collagen (converted collagen/total collagen) is above 20%, the final skin product will lack a fibrous appearance and toughness. However if rehydration is insufficient the helical structure of collagen can't be destroyed sufficiently in the next heat treatment step and thus the skin cannot be softened. Theoretically, there is 74.5% α-helical configuration but no β-sheet in the advanced structure of collagen protein, thus toughness is sufficient and brittleness is insufficient. There is 66.3% β-sheet but no α-helical structure in gelatin, thus it is brittle and lacks toughness. If water content is above 50% before steam heating, too much collagen will be converted into gelatin in the process of steam heating, and then the final artificial skin will be very brittle and be not tough enough. For pigskin there are two reference points for the relationship between the water content of rehydrated skin and the conversion ratio of collagen: (1) if a skin containing 40 wt % water is heated at 100° C. for 5 min, the softening degree of heated skin will be 5% of the rehydrated skin and the conversion ratio of collagen will be 6%; (2) if a skin containing 50 wt % water is heated at 125° C. for 45 min, the softening degree will be 95% and conversion ratio of collagen will be 50%. Therefore, in the present invention, it is preferred that the skin containing 45 wt % water s heated at 110° C. for 20 min, and then the softening degree will be about 65% and conversion rate of collagen will be about 15%.

When the softened skin obtained through the above-described treatment is mixed with water (the weight ratio of the skin to water is 1:2) and grinded into a slurry, the content of α-helix is more than 50%, the content of β-sheet is less than 20% and the efficiency of grinding increases by 2.5 times. If the dry skin is grinded directly without being softened through the above-described treatment it will have, not only, lower grinding efficiency but also higher energy dissipation due to the solid triple helical structure of collagen protein The temperature of the slurry will be very high (even above 60° C.) and change the structure of collagen (this occurs when the temperature is higher than 42° C.) and this will lead to loss of the value of reorganized skin.

Some additives can be added into the slurry for better nutrition and taste when the method in the invention is used to produce pet foods or pet toys. For example, at 20-90° C. (to prevent solidification of the slurry), poultry, fish, vegetables, fruits, vegetable juice and fruit juice can be added into the slurry. It is preferred that the weight of additives is not more than 70% of the total weight of the softened wet skin. Spices and essence can also be added into the slurry. Condiment can also be added into the slurry, such as salt, sugar, glucose, cheese, cocoa powder, honey, monosodium glutamate, hydrolyzed plant protein, yeast extract, etc. Drug ingredients can also be added into the slurry as well, such as traditional Chinese medicine powders, which can be selected from mint, glycyrrhizin, tea, honeysuckle, etc. These traditional Chinese medicine powders have certain medicinal effect, e.g. refreshing breath and reducing internal heat, thus the pet foods containing them can be helpful for pet's (e.g., dog's) oral health.

The applicant also found that the cross-link of collagen protein will be promoted when the enzymes which can catalyze the transfer reaction of acetyl and aldehyde, especially transglutaminase, are added into the slurry. It is preferred that the weight of the added enzymes is not more than 3.5% of the total weight of the softened wet skin.

The applicant also found that when sodium alginate and $Ca^{2+}$ are added into the slurry, a gelation reaction between sodium alginate and $Ca^{2+}$ (calcium alginate is produced) will further promote the gelation of the slurry and improve toughness and tension strength of the final products Then products with porous fiber structure will be formed. It is preferred that the weight of the sodium alginate is 0.10-2.0% of the total weight of the softened wet skin. Concentration of $Ca^{2+}$ at 50-500 ppm is preferred. Additionally, sodium alginate can be added into the slurry firstly, and then the products which are in form of gel or solid state will react in water bath (containing $Ca^{2+}$) for 0.5-10 min. Herein, the preferred $Ca^{2+}$ is $CaCl_2$.

In general cases, when the enzymes which can promote crosslink of collagen protein are added into the grinded slurry, the slurry will form a gel mixture. Before the final solid products are formed, the gel mixture can be added in the twin screw extruder and then the twin screw extruder is operated to extrude the gel mixture. Two benefits are that: (1) the said gel mixture can be formed to a certain shaped product. For example, the said gel mixture can be extruded and placed on a plate to get sheet solid products which can be used as packing materials. In another example, the gel mixture can be extruded into a pre-shaped molds to obtain a final product of any shape. (2) Toughness and tension strength of the final products are further improved because the gel mixture is extruded in twin screw extruder. To further strengthen the extrusion effect, the screw of the twin screw extruder can be lengthened (e.g. the length of the screw is two times the length of conventional twin screw extruder) in accordance with the requirement of the final product.

After the gel mixture is extruded and formed to a certain shape, it can be placed for a period to solidify. It can be dried and dewatered and the solid products in a certain shape are obtained. As mentioned above, when the sodium alginate has been added into the slurry the products can be placed in a water bath containing $Ca^{2+}$ to be gelatinized, so as to improve tensile strength of the reorganized skin.

In addition, pet food and pet toys can be manufactured from the solid products provided in this invention. For example, the gel mixture can be placed on the plate to get sheet solid product and this can be used as pet food. The said gel mixture can also be filled in a pre-shaped mold, and the final solid product has a stereoscopic shape, such as cone, star, or spherical shape. Pets, such as dogs, can be attracted by these shapes. Moreover, the solid product can be processed into more complicated shapes when the product is manufactured into a pet toy. For example, as shown in FIG. 1, the whole shape of the pet toy is a cylinder, and there are several (such as, ten or more) wave-shaped ridges on the surface thereof. These wave-shaped ridges can be bitten by the pet as well as the toy being used for pet food.

Details of the method of processing animal skin in the invention are specified in the following examples.

Example 1

1) Dry animal skin (water content is 7-38 wt %, and the dry animal skin is bovine hide or pigskin, which has been defatted, dried and contains collagenous fibers) is selected and soaked in 0-55° C. water for rehydration until the water content is 40-50 wt %. Subsequently, the dry animal skin is treated by hot steam at 100-125° C. for 5-45 min. It is then cooled to 35-5° C. using a water spray, and the pH is adjusted to 4.7-5.3, and then a softened wet skin is obtained.

2) The softened wet skin is rinsed with and mixed with water and then the mixture is grinded to a slurry. The weight ratio of the softened wet skin to the water is 1:2.

3) Fragments of poultry, fish, meat, vegetables, fruits, and for vegetable juice, fruit juice are added into the slurry obtained in step 2) at 20-90° C. The weight of the added fragments is no more than 70% of the total weight of the softened wet skin. Sodium alginate is also added and the weight of the added Sodium alginate is between 0.10-2.0% of the total weight of the slurry.

4) Transglutaminase (TGase) is then added at 20-70° C. The mixture is vacuum-degassed and a gel mixture forms. The weight of the added transglutaminase is no more than 3.5% of the total weight of the softened wet skin.

5) The gel mixture obtained in step 4) is extruded out through a twin screw extruder and then placed on a horizontal flat plate and then the whole, wet reorganized skin is obtained.

6) The extruded reorganized skin is gelatinized in a water bath containing $CaCl_2$ (concentration of $CaCl_2$ is 50-500 ppm) for 0.5-10 min to strengthen the tensile strength of the reorganized skin.

7) A one millimeter thick reorganized skin is obtained by drying and dewatering. Drying is performed at 50-70° C. for 100-200 min and the humidity is no more than 30%.

Example 2

1) Dry pig skin (water content is about 10 wt %, and the pig skin is defatted and dried and contains collagenous fibers) is selected and soaked in 55° C. water and rehydrated until the water content is about 40%. Subsequently, the pigskin is treated by hot steam at 100-125° C. for about 45 min, it is then cooled to 25° C. using a water spray, and the pH is adjusted to about 5, and then softened wet skin is obtained.

2) The softened wet skin is rinsed and mixed with water and then the mixture is grinded to a slurry. The weight ratio of the softened wet skin to the water is 1:2.

3) Fragments of poultry, fish, meat, vegetables, fruits, and/or vegetable juice, fruit juice are added into the slurry obtained in step 2) at about 60° C. The weight of the added fragments is no more than 60% of the total weight of the softened wet skin. Sodium alginate is also added and the weight of the added Sodium alginate is 1.0% of the total weight of the slurry.

4) Transglutaminase (TGase) is then added at 60° C. The mixture is vacuum-degassed and a gel mixture forms. The weight of the added transglutaminase is 3.5% of the total weight of the softened wet skin.

5) The gel mixture obtained in step 4) is extruded out through a twin screw extruder and then placed on a horizontal flat plate and then the whole wet reorganized skin is obtained.

6) The extruded reorganized skin is gelatinized in water bath containing $CaCl_2$ (concentration of $CaCl_2$ is about 300 ppm) for 10 min, to strengthen the tensile strength of the reorganized skin.

7) A one millimeter thick reorganized skin is obtained by drying and dewatering. Drying is performed at about 70° C. for 200 min and the humidity is about 20%.

Figure 2:
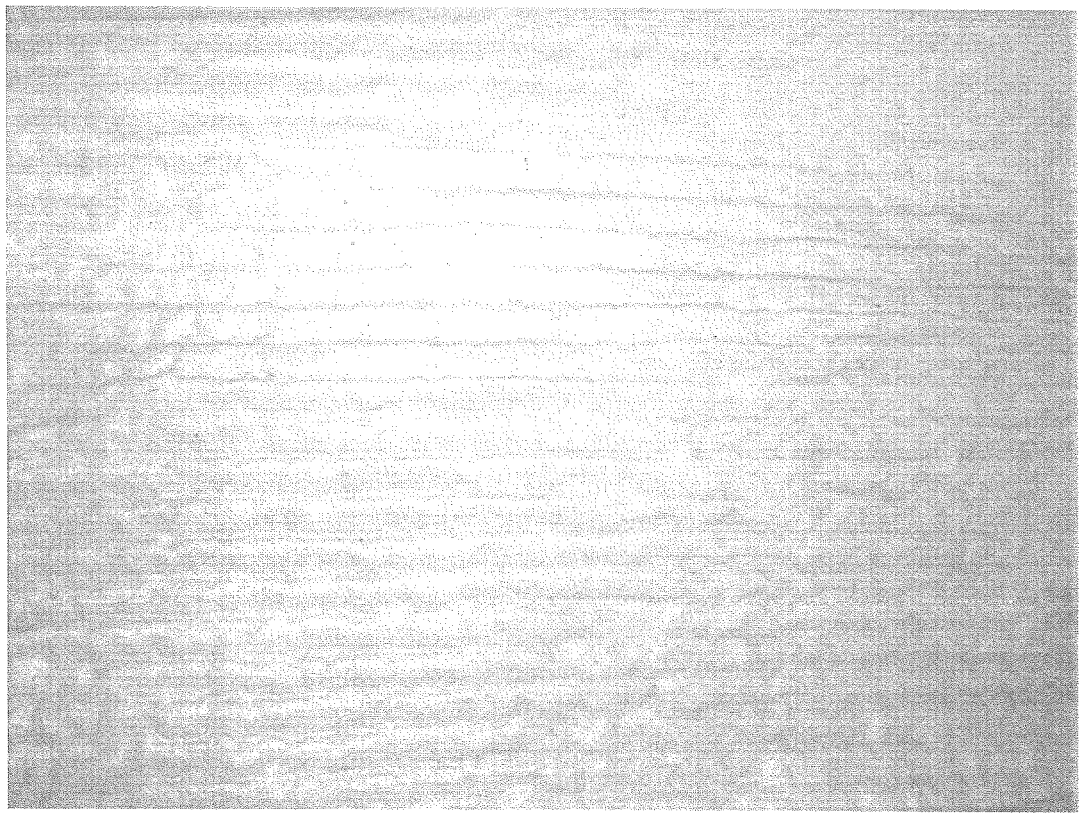
FIG. 2 is a picture of the reorganized skin produced in an example in the invention.

The obtained reorganized skin is illustrated in FIG. 2 and its flexibility and tensile strength are similar with the natural skin.

Preferred embodiments of the invention are described in details above. It should be understood that a skilled person can conceive various modifications and variations without creativity, according the new method/invention. Thus, all technical solutions derived from the present invention's method using logical analysis, reasoning or limited experiments based on prior experience shall be within the protection scope claimed in the claims.

What is claimed is:

1. A method of processing animal skin, comprising the steps of:
    1) providing a dry animal skin containing 7-38 wt % water;
    2) rehydrating and softening the said dry animal skin to obtain a softened wet skin;
    3) mixing the softened wet skin with water to obtain a mixture, and grinding the mixture to a slurry;
    4) obtaining a solid product through a cross-link of collagen proteins in the said slurry;
    wherein, the said rehydrating in step 2) is done by soaking the dry animal skin in 0-55° C. water until the animal skin contains 40-50 wt % water obtain a rehydrated animal skin; and
    the said softening in step 2) comprises a step of heating the rehydrated animal skin;
    wherein, the heating is performed in hot steam at 100~125° C. for 5~45 min.

2. The method as claimed in claim 1, wherein, the dry animal skin is a defatted and dried animal skin containing collagen fibers.

3. The method as claimed in claim 2, wherein, the dry animal skin is pigskin.

4. The method as claimed in claim 1, wherein, the water content of the dry animal skin is about 45% after rehydration, and the dry animal skin containing about 45 wt % water is treated by hot steam at about 110° C. for about 20 min after rehydration.

5. The method as claimed in claim 1, wherein, in step 3), the weight ratio of the softened wet skin to the water is 1:2.

6. The method as claimed in claim 1, wherein, in the slurry, the α-helix content in collagen protein is more than 50%, and the β-sheet content is less than 20%.

7. The method as claimed in claim 1, wherein, after the said softened wet skin is grinded to a slurry, additives are added into the slurry for nutrition and tastes.

8. The method as claimed in claim 1, wherein, after the said softened wet skin is ground to a slurry, traditional Chinese medicine powders are added into the slurry.

9. The method as claimed in claim 8, wherein, the said traditional Chinese medicine powders are selected from: mint, glycyrrhizin, tea and honeysuckle.

10. The method as claimed in claim 1, wherein, after the said softened wet skin is ground to slurry, an enzyme catalyzing transfer reaction of acetyl and aldehyde is added into the said slurry.

11. The method as claimed in claim 10, wherein, the said enzyme catalyzing transfer reaction of acetyl and aldehyde is transglutaminase.

12. The method as claimed in claim 11, wherein, after the said softened wet skin is ground to slurry, sodium alginate and $Ca^{2+}$ are added into the slurry.

13. A method of processing animal skin, comprising the steps of:
1) dry animal skin being selected and soaked in 0-55° C. water for rehydration until the water content reaches 40-50 wt %, and subsequently treated by hot steam at 100-125° C. for 5-45 min, followed by being cooled to 35-50° C. through water spray, and pH being adjusted to 4.7-5.3, and then a softened wet skin being obtained;
2) the softened wet skin being rinsed and mixed with water and then the mixture being grinded to a slurry, wherein the weight ratio of the softened wet skin to the water is 1:2;
3) fragments of poultry, fish, meat, vegetables, fruits, and/or vegetable juice, fruit juice being added into the slurry obtained in step 2) at 20-90° C.; and then sodium alginate being added, wherein the weight of the added fragments is not more than 70% of the total weight of the softened wet skin and the weight of the added sodium alginate is 0.10-2.0% of the total weight of the slurry;
4) transglutaminase being added at 20-700 and the mixture being vacuum-degassed to form a gel mixture, wherein the weight of the added transglutaminase is not more than 3.5% of the total weight of the softened wet skin;
5) the gel mixture obtained in step 4) being extruded out through a twin screw extruder and then placed on a horizontal flat plate and an extruded reorganized skin being obtained;
6) the extruded reorganized skin being gelatinized in water bath containing $CaCl_2$ for 0.5-10 min, wherein the concentration of the $CaCl_2$ is 50-500 ppm;
7) a one millimeter thick reorganized skin being obtained after drying and dewatering, wherein and the drying is performed at 50-70° C. for 100-200 min and the humidity is not more than 30%.

* * * * *